(12) United States Patent
Vile et al.

(10) Patent No.: US 10,849,964 B2
(45) Date of Patent: Dec. 1, 2020

(54) METHODS AND MATERIALS FOR TREATING CANCER

(71) Applicants: Mayo Foundation for Medical Education and Research, Rochester, MN (US); Leeds University, Leeds (GB)

(72) Inventors: Richard G. Vile, Rochester, MN (US); Timothy J. Kottke, Oronoco, MN (US); Jose S. Pulido, Rochester, MN (US); Alan A. Melcher, Leeds (GB); Peter Selby, Leeds (GB)

(73) Assignees: Mayo Foundation for Medical Education and Research, Rochester, MN (US); Leeds University, Leeds (GB)

( * ) Notice: Subject to any disclaimer, the term of this patent is extended or adjusted under 35 U.S.C. 154(b) by 344 days.

(21) Appl. No.: 16/011,416

(22) Filed: Jun. 18, 2018

(65) Prior Publication Data
US 2019/0015489 A1 Jan. 17, 2019

Related U.S. Application Data

(62) Division of application No. 13/578,224, filed as application No. PCT/US2011/024397 on Feb. 10, 2011, now Pat. No. 10,022,431.

(60) Provisional application No. 61/303,222, filed on Feb. 10, 2010.

(51) Int. Cl.
| | | |
|---|---|---|
| A61K 39/00 | (2006.01) | |
| A61K 35/766 | (2015.01) | |
| A61P 35/00 | (2006.01) | |

(52) U.S. Cl.
CPC ........ *A61K 39/0011* (2013.01); *A61K 35/766* (2013.01); *A61P 35/00* (2018.01); *A61K 2039/5256* (2013.01); *A61K 2039/53* (2013.01); *A61K 2039/54* (2013.01); *A61K 2039/55516* (2013.01); *C12N 2760/20232* (2013.01); *C12N 2760/20243* (2013.01)

(58) Field of Classification Search
CPC ................................................ A61K 39/0011
USPC ........................................................... 506/9
See application file for complete search history.

(56) References Cited

U.S. PATENT DOCUMENTS

| | | | |
|---|---|---|---|
| 5,695,963 | A | 12/1997 | McKnight et al. |
| 6,140,053 | A | 10/2000 | Koster |
| 9,517,258 | B2 | 12/2016 | Pulido et al. |
| 10,022,431 | B2 | 7/2018 | Vile et al. |
| 10,029,003 | B2 | 7/2018 | Pulido et al. |
| 2010/0121033 | A1 | 5/2010 | Camphausen et al. |
| 2010/0129389 | A1 | 5/2010 | Ware et al. |
| 2010/0168206 | A1 | 7/2010 | Gollob et al. |
| 2010/0221349 | A1 | 9/2010 | Fuller |
| 2012/0258046 | A1 | 10/2012 | Mutzke |
| 2012/0308484 | A1 | 12/2012 | Szalay et al. |
| 2012/0308601 | A1 | 12/2012 | Vile et al. |
| 2013/0287772 | A1 | 10/2013 | Halbert et al. |
| 2015/0064218 | A1 | 3/2015 | Pulido et al. |
| 2017/0080065 | A1 | 3/2017 | Pulido et al. |
| 2017/0080066 | A1 | 3/2017 | Vile et al. |
| 2017/0143813 | A1 | 5/2017 | Pulido et al. |

FOREIGN PATENT DOCUMENTS

| | | |
|---|---|---|
| WO | WO 2008/109825 | 9/2008 |
| WO | WO 2011/100468 | 8/2011 |
| WO | WO 2013/036201 | 3/2013 |
| WO | WO 2013/138697 | 9/2013 |
| WO | WO 2013/173223 | 11/2013 |
| WO | WO 2013/178344 | 12/2013 |

OTHER PUBLICATIONS

U.S. Appl. No. 13/578,224, filed Aug. 9, 2012, Vile et al.
U.S. Appl. No. 14/385,240, filed Sep. 15, 2014, Pulido et al.
U.S. Appl. No. 15/126,333, filed Sep. 15, 2016, Pulido et al.
U.S. Appl. No. 15/126,338, filed Sep. 15, 2016, Vile et al.
U.S. Appl. No. 15/359,333, filed Nov. 22, 2016, Pulido et al.
GenBank® Accession No. NP_061820, GI: 11128019, "cytochrome c [*Homo sapiens*]," Mar. 11, 2011, 2 pages.
GenBank® Accession No. NW_004078038.1, "*Homo sapiens* chromosome 9 genomic scaffold, alternate assembly CHM1_1.0, whole genome shotgun sequence," Nov. 2, 2012, 4 pages.
GenBank® Accession No. U40038.1 GI: 1181670, "Human GTP-binding protein alpha q subunit (GNAQ) mRNA, complete cds," Feb. 7, 1996, 2 pages.
GenBank® Accession No. V00568 GI: 34815, "Human mRNA encoding the c-myc oncogene," Oct. 7, 2008, 2 pages.
GenBank® Accession No. X02812 GI: 37092, "Human mRNA for transforming growth factor-beta (TGF-beta)," Mar. 27, 1995, 2 pages.
GenBank® Accession No. X51420.1 GI: 37512, "*Homo sapiens* mRNA for tyrosinase-related protein precursor (TYRP1)," Oct. 7, 2008, 2 pages.
GenBank® Accession No. X57621.1 GI: 55450, "M.musculus YB-1 mRNA," Apr. 18, 2005, 2 pages.
GenBank® Accession No. X58723 GI: 34522, "Human MDR1 (multidrug resistance) gene for P-glycoprotein," Nov. 14, 2006, 2 pages.
GenBank® Accession No. XM_001002680 GI: 255708374, "PREDICTED: Mus musculus ATP-binding cassette, sub-family B (MDR/TAP), member 5 (Abcb5), mRNA," Jun. 20, 2007, 2 pages.
GenBank® Accession No. XM_005250045.1 GI: 530387105, "PREDICTED: *Homo sapiens* v-raf murine sarcoma viral oncogene homolog B (BRAF), transcript variant X1, mRNA," Aug. 13, 2013, 4 pages.

(Continued)

*Primary Examiner* — Karla A Dines
(74) *Attorney, Agent, or Firm* — Fish & Richardson P.C.

(57) ABSTRACT

This document provides methods and materials related to treating cancer. For example, methods and materials for using nucleic acid libraries to treat cancer are provided.

18 Claims, 13 Drawing Sheets

(56) References Cited

OTHER PUBLICATIONS

GenBank® Accession No. XM_005250046.1 GI: 530387107, "PREDICTED: *Homo sapiens* v-raf murine sarcoma viral oncogene homolog B (BRAF), transcript variant X2, mRNA," Aug. 13, 2013, 4 pages.
GenBank® Accession No. XM_005250047.1 GI: 530387109, "PREDICTED: *Homo sapiens* v-raf murine sarcoma viral oncogene homolog B (BRAF), transcript variant X3, mRNA," 2 pages.
GenBank® Accession No. XM_005251574.1 GI: 530390132, "PREDICTED: *Homo sapiens* tyrosinase-related protein 1 (TYRP1), transcript variant X1, mRNA," Feb. 3, 2014, 3 pages.
GenBank® Accession No. XM_005270904.1 GI: 530362706, "PREDICTED: *Homo sapiens* Y box binding protein 1 (YBX1), transcript variant X1, mRNA," Aug. 13, 2013, 2 pages.
"A Randomized Study of Nivolumab Versus Bevacizumab and a Safety Study of Nivolumab in Adult Subjects With Recurrent Glioblastoma (GBM) (CheckMate 143)," Clinical Trials.gov [online] Dec. 2014, [retrieved on Mar. 18, 2015]. Retrieved from the Internet: <URL: https://clinicaltrials.gov/ct2/show/NCT02017717>, 3 pages.
"Nucleic Acids and Protein Calculations: DNA Molar Conversions," printed from http://www.genscript.com/converstion.html, as p. 1/1 on Apr. 24, 2017.
"UniProt entry P08183—MDR1_HUMAN: Multidrug resistance protein 1," Aug. 1, 1988, pp. 1-12. Retrieved from the Internet: <http://www.uniprot.org/uniprot/P08183#pathology_and_biotech> on Jun. 3, 2015.
"UniProt entry P35968—VGFR2_HUMAN: Vascular endothelial growth factor receptor 2," Jun. 1, 1994, pp. 1-8. Retrieved from the Internet: <http://www.uniprot.org/uniprot/P35968> on Jun. 3, 2015.
"Using Viro/Immunotherapy to Target Stem-Like Cells of Tumor Recurrence," Oncolytic Viruses and Stem Cell Workshop, National Cancer Institute (NCI), Washington D.C., Sep. 6, 2013, [slideshow] 51 pages.
Ahmad et al., "Optimised electroporation mediated DNA vaccination for treatment of prostate cancer," *Genetics Vaccines and Therapy*, 8:1, pp. 1-13, Feb. 5, 2010.
Alonso-Camino et al., "The profile of tumor antigens which can be targeted by immunotherapy depends upon the tumor's anatomical site," *Mol. Ther.*, 22(11):1936-1948, Nov. 2014.
Anonymous: "Programme replicating oncolytic virus therapeutics 2013," Jun. 1, 2013, pp. 1-5, Retrieved from the Internet: URL: http://www.iovmc.org/2013/programme/ Retrieved on Sep. 14, 2017.
Avogadri and Wolchok., "Selecting antigens for cancer vaccines," Nat. Biotechnol. 30(4):328-329, Apr. 10, 2012.
Barry et al., "Expression library immunization to discover and improve vaccine antigens," *Immunol Rev.*, 199:68-83, Jun. 2004.
Baxevanis et al., "Cancer immunotherapy," *Crit Rev Clin Lab Sci.*, 46(4): 167-189, 2009.
Boisgerault et al., "Functional cloning of recurrence-specific antigens identifies molecular targets to treat tumor relapse," *Mol. Ther.*, 21(8):1507-1516, Epub Jun. 11, 2013.
Bridle et al., "Vesicular stomatitis virus as a novel cancer vaccine vector to prime antitumor immunity amenable to rapid boosting with adenovirus," Mol. Ther., 17(10):1814-1821, Oct. 2009.
Chen et al., "Principal expression of two mRNA isoforms (ABCB 5alpha and ABCB 5beta ) of the ATP-binding cassette transporter gene ABCB 5 in melanoma cells and melanocytes," *Pigment Cell Res.*, 18(2):102-112, Apr. 2005 [author manuscript].
Cho et al., "A potent vaccination strategy that circumvents lymphodepletion for effective antitumor adoptive T-cell therapy," *Cancer Res.*, 72:1986-1995, Apr. 15, 2012.
Chong et al., "Expression of co-stimulatory molecules by tumor cells decreases tumorigenicity but may also reduce systemic antitumor immunity," *Hum Gene Ther.*, 7(14):1771-1779, Sep. 10, 1996.
Cluff, "Monophosphoryl Lipid A (MPL) as an Adjuvant for Anit-Cancer Vaccines: Clinical Results," *Lipid A in Cancer Therapy*, Landes Bioscience and Springer Science and Business Media, Chpt. 10, pp. 111-123, 2009.

Daniels et al., "A simple method to cure established tumors by inflammatory killing of normal cells," Nature Biol., 22(9):1125-1132, Epub Aug. 2004.
De GruijI et al., "Whole-cell cancer vaccination: from autologous to allogeneic tumor- and dendritic cell-based vaccines," *Cancer Immunology Immunotherapy.*, 57:1569-1577, 2008.
Diaz et al., "Oncolytic immunovirotherapy for melanoma using vesicular stomatitis virus," Cancer Res., 67(6):2840-2848 Mar. 2007.
Drape et al., "Epidermal DNA vaccine for influenza is immunogenic in humans," *Vaccine.*, 24:4475-4481, 2006.
Ebert et al., "Systemic therapy of experimental breast cancer metastases by mutant vesicular stomatitis virus in immune-competent mice," Cancer Gene Ther., 12(4):350-358, Apr. 2005.
Fernandez et al., "Genetically engineered vesicular stomatitis virus in gene therapy: application for treatment of malignant disease," J. Virol., 76(2):895-904, Jan. 2002.
Ferrone, "Immunotherapy dispenses with tumor antigens," Nature Biotech., 2004, 22(9):1096-1098.
Francisco et al., "Chapter 4: Melanoma. Genetics: From Susceptibility to Progression," Melanoma—From Early Detection to Treatment, Dr. Ht Duc (Ed.), pp. 83-136. Retrieved from the Internet: <http://www.intechopen.com/books/melanoma-from-early-detection-to-treatment/melanoma-genetics-from-susceptibility-to-progression> Jan. 2013.
Galivo et al., "Interference of CD40L-mediated tumor immunotherapy by oncolytic vesicular stomatitis virus," Human Gene Ther., 21(4):439-450, Apr. 2010.
Galivo et al., "Single-cycle viral gene expression, rather than progressive replication and oncolysis, is required for VSV therapy of B16 melanoma," Gene Ther., 17(2):158-170, print Feb. 2010, Epub Dec. 2009.
Gessi et al., "GNA11 and N-RAS mutations: alternatives for MAPK pathway activating GNAQ mutations in primary melanocytic tumors of the central nervous system," *Neuropathology Applied Neurobiology*, 39(4):417-425, Apr. 25, 2013.
Hall and Brown, "Human N-ras: cDNA cloning and gene structure," Nucleic Acids Res., 13(14):5255-5268, Jul. 1985.
Heim, "Normal high resolution karyotypes in patients with adenomatosis of the colon and rectum," *Hereditas.*, 102(2):171-175, 1985.
Hogquist et al., "T cell receptor antagonist peptides induce positive selection," Cell, 76(1):17-27, Jan. 1994.
Jenks et al., "Safety studies on intrahepatic or intratumoral injection of oncolytic vesicular stomatitis virus expressing interferon-beta in rodents and nonhuman primates," *Hum. Gene Ther.*, 21(4):451-462, Apr. 2010.
Joseph et al., "Association of the autoimmune disease scleroderma with an immunologic response to cancer," *Science*, 343(6167):152-157, Epub Dec. 5, 2013.
Kaluza et al., "Adoptive transfer of cytotoxic T lymphocytes targeting two different antigens limits antigen loss and tumor escape," *Hum Gene Ther.*, 23(10):1054-1064, Epub Aug. 13, 2012.
Kottke et al., "Broad antigenic coverage induced by vaccination with virus-based cDNA libraries cures established tumors," *Nature Medicine.*, 17(7):854-860, Jul. 2011.
Kottke et al., "Antitumor immunity can be uncoupled from autoimmunity following heat shock protein 70-mediated inflammatory killing of normal pancreas," Cancer Res., 69(19):7767-1774, Oct. 2009.
Kottke et al., "Induction of hsp70-mediated Th17 autoimmunity can be exploited as immunotherapy for metastatic prostate cancer," Cancer Res., 67(24):11970-11979, Dec. 2007.
Lawson et al., "Recombinant vesicular stomatitis viruses from DNA," *PNAS*, 92(10):4477-4481, May 9, 1995.
Lee et al., "A comprehensive guide to the MAGE family of ubiquitin ligases," *J Mol Biol.*, 429:1114-1142, Apr. 2017.
Linardakis et al., "Enhancing the efficacy of a weak allogeneic melanoma vaccine by viral fusogenic membrane glycoprotein-mediated tumor cell-tumor cell fusion," Cancer Res., 62(19): 5495-5504, Oct. 2002.
Lucas et al., "A new MAGE gene with ubiquitous expression does not code for known MAGE antigens recognized by T cells," *Cancer Research.*, 59:4100-4103, Aug. 15, 1999.

(56) References Cited

OTHER PUBLICATIONS

Obuchi et al., "Development of recombinant vesicular stomatitis viruses that exploit defects in host defense to augment specific oncolytic activity," *J. Virol.*, 77(16):8843-8856, Aug. 2003.
Overwijk et al., "Tumor regression and autoimmunity after reversal of a functionally tolerant state of self-reactive CD8+ T cells," *J. Exp. Med.*, 198(4):569-580, Aug. 2003.
Pulido et al., "Using virally expressed melanoma cDNA libraries to identify tumor-associated antigens that cure melanoma," *Nat Biotechnol.*, 30(4):337-343, Mar. 18, 2012.
Radvanyi, "Immunotherapy Exposes Cancer Stem Cell Resistance and a New Synthetic Lethality," *Mol. Ther.* 21:1472-1474, Aug. 2013.
Ramsburg et al., "A vesicular stomatitis virus recombinant expressing granulocyte-macrophage colony-stimulating factor induces enhanced T-cell responses and is highly attenuated for replication in animals," *J. Virol.*, 79(24):15043-15053, Dec. 2005.
Rochard et al., "Genetic immunization with plasmid DNA mediated by electrotransfer," *Human Gene Therapy.*, 22:789-798, Jul. 2011.
Roda et al., "Stabilization of HIF-2α induces sVEGFR-1 production from tumor-associated macrophages and decreases tumor growth in a murine melanoma model," *J. Immunol.*, 189(6):3168-3177, Sep. 15, 2012.
Rommelfanger et al., "Systemic combination virotherapy for melanoma with tumor antigen-expressing vesicular stomatitis virus and adoptive T-cell transfer," *Cancer Res.*, 72(18):4753-4764, Sep. 15, 2012.
Sang et al. Melanoma-associated antigen genes—An update. Cancer Letters, vol. 302, pp. 85-90, 2011. (Year: 2011).
Sausville and Burger, "Contributions of human tumor xenografts to anticancer drug development," *Cancer Res*, 66(7): 3351-3354, Apr. 2006.
Shakhova et al., "Sox10 promotes the formation and maintenance of giant congenital naevi and melanoma," *Nat. Cell Biol.*, 14(8):882-890, Aug. 2012.
Shibata et al., "Downstream region of the human tyrosinase-related protein gene enhances its promoter activity," Biochem. Biophys. Res. Commun., 184(2):568-575, Apr. 1992.
Srivastava, "Immunotherapy of human cancer: lessons from mice," *Nat Immunol.*, 1(5):363-366, Nov. 2005.
Steitz et al., "Genetic immunization of mice with human tyrosinase-related protein 2: Implications for the immunotherapy of melanoma," *International Journal of Cancer.*, 86:89-94, 2000.
Suzuki et al., "Structural organization of the human mitochondrial cytochrome c1 gene," *J. Biol. Chem.*, 264(3):1368-1374, Jan. 1989.
Thomas and Massagué, "TGF-beta directly targets cytotoxic T cell functions during tumor evasion of immune surveillance.," *Cancer Cell*, 8(5):369-380, Nov. 2005.
Tseng et al., "Letter to the Editor: Long-term survivors after immunotherapy for metastatic melanoma," *Immunology Letters.*, vol. 139:117-118, Feb. 2011.
Van Belle et al., "Melanoma-associated expression of transforming growth factor-beta isoforms," *Am J Pathol.*, 148(6):1887-1894, Jun. 1996.
Vinals et al., "Using in silico transcriptomics to search for tumor-associated antigens for immunotherapy," *Vaccine*, 19(17-19):2607-2614, Mar. 21, 2001.
Wagner et al., "Targeted nucleic acid delivery into tumors: new avenues for cancer therapy," *Biomed Pharmacother.*, 58(3):152-161, Apr. 2004.

Willmon et al., "Vesicular stomatitis virus-induced immune suppressor cells generate antagonism between intratumoral oncolytic virus and cyclophosphamide," Mol. Ther., 19(1):140-149, Jan. 2010.
Wongthida et al., "VSV oncolytic virotherapy in the B16 model depends upon intact MyD88 signaling," Mol. Ther., 19(1):150-158, Jan. 2011.
Woodman "Metastatic uveal melanoma: biology and emerging treatments," *Cancer J.*, 18(2):148-152, Mar.-Apr. 2012, available Feb. 26, 2014.
Yang et al., "Dendritic cell-directed lentivector vaccine induces antigen-specific immune responses against murine melanoma," *Cancer Gene Therapy.*, 18:370-380, 2011.
Yoshida et al., "Development of gene therapy to target pancreatic cancer," *Cancer Sci.*, 95(4): 283-289, Apr. 2002.
Zhuang et al., "C-MYC overexpression is required for continuous suppression of oncogene-induced senescence in melanoma cells," *Oncogene*, 27(52):6623-6634, Nov. 6, 2008.
European Search Report for Application No. 11742816.9 dated Jul. 10, 2013, 8 pages.
European Search Report for Application No. 13760532.5, dated Oct. 20, 2015, 14 pages.
Extended European Search report for International Application No. EP15765847.7, dated Oct. 13, 2017, 7 pages.
Extended European Search Report in International Application No. EP15765220.7, dated Jan. 29, 2018, 22 pages.
International Preliminary Report on Patentability for PCT/US2013/031953 dated Sep. 25, 2014, 6 pages.
International Preliminary Report on Patentability for PCT/US2015/021574, dated Sep. 29, 2016, 14 pages.
International Preliminary Report on Patentability for PCT/US2015/021576, dated Sep. 29, 2016, 10 pages.
International Preliminary Report on Patentability in Application No. PCT/US2011/024397, dated Aug. 23, 2012, 6 pages.
International Search Report and Written Opinion for Application No. PCT/US2013/031953, dated Jul. 4, 2013, 8 pages.
International Search Report and Written Opinion in Application No. PCT/US2011/024397, dated Oct. 25, 2011, 10 pages.
International Search Report and Written Opinion in Application No. PCT/US2015/021574, dated Jul. 8, 2015, 23 pages.
International Search Report and Written Opinion in Application No. PCT/US2015/021576, dated Jul. 10, 2015, 13 pages.
Office Action for European Application No. 11742816.9, dated Apr. 14, 2016, 5 pages.
Office Action for European Application No. 11742816.9, dated Nov. 27, 2017, 4 pages.
Office Action for U.S. Appl. No. 13/578,224 dated Dec. 27, 2013, 17 pages.
Office Action for U.S. Appl. No. 13/578,224 dated Dec. 4, 2014, 14 pages.
Office Action for U.S. Appl. No. 13/578,224 dated Jun. 5, 2015, 14 pages.
Office Action for U.S. Appl. No. 13/578,224 dated May 8, 2013, 14 pages.
Office Action for U.S. Appl. No. 13/578,224 dated Sep. 24, 2015, 16 pages.
Office Action for U.S. Appl. No. 13/578,224, dated Jun. 3, 2016, 14 pages.
Office Action for U.S. Appl. No. 14/385,240, dated Mar. 18, 2016, 14 pages.
Partial Supplementary European Search Report for International Application No. 15765220.7, dated Oct. 23, 2017, 26 pages.

TC2 Tumor from Mouse
treated with VSV-GFP

TC2 Tumor from Mouse
treated with OSOVIASAL

TC2 Tumor from Mouse treated with VSV-GFP

TC2 Tumor from Mouse treated with OSOVIASAL

TC2 Tumor from Mouse treated with VSV-GFP

Sheets of tumor cells with no detectable inflammatory infiltrate

TC2 Tumor from Mouse treated with OSOVIASAL

Tumor cells arranged in nests
Extensive interstitial infiltrate of lymphocytes

Control Injection (PBS)

Normal Limits
10x

Figure 9B

VSV-OSOVIASAL Intraprostatic Injection – Lymphoplasmacytic cells in stromal tissue

METHODS AND MATERIALS FOR TREATING CANCER

CROSS-REFERENCE TO RELATED APPLICATIONS

This application is a divisional application of U.S. Ser. No. 13/578,224, filed Aug. 9, 2012 (now U.S. Pat. No. 10,022,431), which is a National Stage application under 35 U.S.C. § 371 and claims benefit of International Application No. PCT/US2011/024397, having an International Filing Date of Feb. 10, 2011, which claims the benefit of U.S. Provisional Application Ser. No. 61/303,222, filed Feb. 10, 2010. The disclosures of the prior applications are considered part of (and are incorporated by reference in) the disclosure of this application.

BACKGROUND

1. Technical Field

This document relates to methods and materials involved in treating cancer. For example, this document provides methods and material for using nucleic acid libraries to treat cancer.

2. Background Information

Cancer is a serious illness that affects many people every year. In general, there are several common methods for treating cancer: surgery, chemotherapy, radiation therapy, immunotherapy, and biologic therapy. When initially diagnosed with cancer, a cancer specialist such as an oncologist can provide a patient with various cancer treatment options. Typically, an oncologist will recommend the best treatment plan based on the type of cancer, how far it has spread, and other important factors like the age and general health of the patient.

SUMMARY

This document provides methods and materials related to treating cancer. For example, this document provides methods and materials for using nucleic acid libraries to treat cancer. As described herein, a nucleic acid library can be used to deliver a large number of the antigens (e.g., polypeptides) that are present in the particular cancer, or in the organ or tissue of origin of the cancer, to a mammal such that the mammal's immune system can develop an immune response against those antigens (e.g., polypeptides) that are expressed by the cancer, thereby causing the cancer to regress. For example, a cDNA expression library designed to express polypeptides from a particular cancer, or the organ or tissue of origin of the cancer, can be engineered into viruses (e.g., an oncolytic virus), and then the engineered viruses can be administered to a patient such that the polypeptides are expressed. This ensuing expression of the cancer-, organ-, or tissue-specific polypeptides in the presence of the inflammation mounted against the virus can cause an immune reaction directed against the cancer, thereby causing the cancer to regress.

If the cancer somehow changes and new antigens are subsequently expressed, then the same nucleic acid library or a different nucleic acid library (e.g., a nucleic acid library generated from the changed cancer cells) can be administered to the mammal. In these cases, the mammal can develop an immune response against those antigens (e.g., polypeptides) that are expressed by the changed cancer, thereby causing the cancer to regress.

In general, one aspect of this document features a method for treating cancer present in a mammal. The method comprises, or consists essentially of, administering, to the mammal, a nucleic acid library under conditions wherein nucleic acid members of the nucleic acid library are expressed in the mammal, thereby reducing the number of viable cancer cells present within the mammal. The mammal can be a human. The administration can be an intratumoral or intravenous administration. The nucleic acid library can be a cDNA library. The nucleic acid library can be administered to the mammal using a virus. The virus can be an oncolytic virus. The virus can be a vesicular stomatitis virus. The nucleic acid members can be cDNA molecules, wherein each cDNA molecule encodes a polypeptide. The nucleic acid library can comprise a plurality of different nucleic acid members, and wherein each of the plurality of different nucleic acid members can encode a different mammalian polypeptide. The different mammalian polypeptides can be polypeptides of a member of the same species as the mammal. The different mammalian polypeptides can be polypeptides of a member of a different species than the species of the mammal. The different mammalian polypeptides can be polypeptides of the mammal. The different mammalian polypeptides can be polypeptides of the cancer. The different mammalian polypeptides can be polypeptides of an organ or tissue that is an organ or tissue of origin of the cancer. The cancer can be prostrate cancer, and the different mammalian polypeptides can be polypeptides expressed by prostate cells. The cancer can be lung cancer, and the different mammalian polypeptides can be polypeptides expressed by lung cells. The cancer can be skin cancer, and the different mammalian polypeptides can be polypeptides expressed by skin cells. The nucleic acid library can comprise a collection of greater than $10^4$ different nucleic acid members, and wherein each of the $10^4$ different nucleic acid members can encode a different mammalian polypeptide. The nucleic acid library can comprise a collection of greater than $10^5$ different nucleic acid members, and wherein each of the $10^5$ different nucleic acid members can encode a different mammalian polypeptide. The nucleic acid library can comprise a collection of greater than $10^6$ different nucleic acid members, and wherein each of the $10^6$ different nucleic acid members can encode a different mammalian polypeptide. The nucleic acid library can comprise a collection of greater than $10^7$ different nucleic acid members, and wherein each of the $10^7$ different nucleic acid members can encode a different mammalian polypeptide. The nucleic acid library can be administered to the mammal in combination with an adjuvant. The adjuvant can be selected from the group consisting of an HSP70 polypeptide, a vesicular stomatitis virus, BCG, a vaccinia virus, and an adenovirus.

In another aspect, this document features a composition for treating cancer present in a mammal. The composition comprises, or consists essentially of, a nucleic acid library comprising a plurality of different nucleic acid members, wherein each of the plurality of different nucleic acid members encodes a different mammalian polypeptide and is located within the genome of an oncolytic virus having the ability to infect a cell present within the mammal, and wherein the mammalian polypeptides are expressed within the mammal following administration of the composition to the mammal. The mammal can be a human. The administration can be an intratumoral or intravenous administration. The nucleic acid library can be a cDNA library. The oncolytic virus can be a vesicular stomatitis virus. The different mammalian polypeptides can be polypeptides of a member of the same species as the mammal. The different mammalian polypeptides can be polypeptides of a member of a different species than the species of the mammal. The different mammalian polypeptides can be polypeptides of the mammal. The different mammalian polypeptides can be polypeptides of the cancer. The different mammalian polypeptides can be polypeptides of an organ or tissue that is an organ or tissue of origin of the cancer. The cancer can be prostrate cancer, and the different mammalian polypeptides can be polypeptides expressed by prostate cells. The cancer can be lung cancer, and the different mammalian polypeptides can be polypeptides expressed by lung cells. The cancer can be skin cancer, and the different mammalian polypeptides can be polypeptides expressed by skin cells. The nucleic acid library can comprise a collection of greater than $10^4$ different nucleic acid members, and wherein each of the $10^4$ different nucleic acid members can encode a different mammalian polypeptide. The nucleic acid library can comprise a collection of greater than $10^5$ different nucleic acid members, and wherein each of the $10^5$ different nucleic acid members can encode a different mammalian polypeptide. The nucleic acid library can comprise a collection of greater than $10^6$ different nucleic acid members, and wherein each of the $10^6$ different nucleic acid members can encode a different mammalian polypeptide. The nucleic acid library can comprise a collection of greater than $10^7$ different nucleic acid members, and wherein each of the $10^7$ different nucleic acid members can encode a different mammalian polypeptide. The composition can lack serum.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 9A and 9B contain photographs of TC2 tumors following intravenous treatment with PBS or OSOVIASAL. Direct intraprostatic injection of OSOVIASAL induced clinical signs of prostatitis.

DETAILED DESCRIPTION

Figure 1:
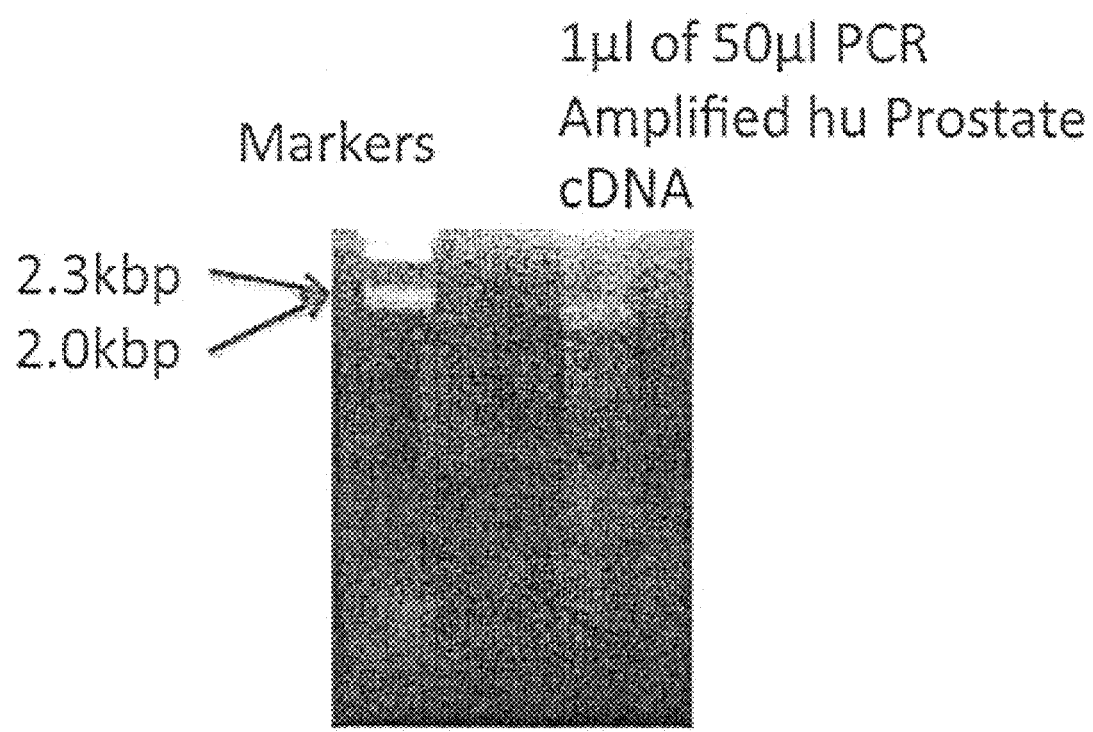
FIG. 1 is a photograph of a gel of a PCR amplified, human prostate cDNA expression library. A Template Bioexpress plasmid was used to carry the cDNAs.

This document provides methods and materials related to the use of nucleic acid libraries to treat cancer. For example, this document provides methods and materials for using nucleic acid libraries to reduce the number of viable cancer cells within a mammal and/or to increase the survival time of a mammal with cancer. Any type of cancer can be treated such that the number of viable cancer cells within the mammal is reduced and/or the survival time of the mammal with cancer is increased. For example, prostate cancer, skin cancer (e.g., melanoma), lung cancer, breast cancer, pancreatic cancer, and colorectal cancer can be treated as described herein.

The term "nucleic acid library" as used herein refers to a collection of nucleic acid molecules where the collection includes at least about $10^2$ different nucleic acid molecules. For example, a nucleic acid library described herein can include at least about $10^2$, $10^3$, $10^4$, $10^5$, $10^6$, $10^7$, or more different nucleic acid molecules. In some cases, a nucleic acid library used as described herein can be a cDNA library. For example, a nucleic acid library can have at least about $10^2$ different cDNA molecules. Each different cDNA molecule can encode a different polypeptide. In general, a nucleic acid library provided herein can be designed to express its nucleic acid members (e.g., cDNAs) such that a collection of at least $10^2$ different polypeptides can be produced. The polypeptides can be full-length polypeptides as found in the source cells used to generate the nucleic acid library or can be portions of such full-length polypeptides. For example, such portions of full-length polypeptides can be polypeptides having greater than 10, 20, 30, 40, 50, 60, 70, 80, 90, 100, or more amino acid residues of the full-length polypeptides.

In general, a nucleic acid library (e.g., an expression nucleic acid library) can be obtained from the cancer to be treated or can be obtained from an organ or tissue or cell (organ/tissue/cell) of origin of the cancer type to be treated. For example, when treating skin cancer (e.g., melanoma), a cDNA library created from normal skin cells can be used. When treating pancreatic cancer, a cDNA library created from normal pancreatic cells can be used. In some cases, a nucleic acid library can be obtained from an embryonic cell or cell line. An embryonic cell library can provide many tumor associated antigens since many tumor associated antigens also are embryonically expressed antigens that become re-activated for expression in tumor cells. In some cases, vaccination with an embryonic cell nucleic acid library can allow for effective vaccination over and above that achieved with vaccination against tissue specific antigens.

In some cases, a nucleic acid library can be a collection of at least about $10^2$ different nucleic acid molecules of the mammal to be treated (e.g., an autoexpression library) or can be a collection of at least about $10^2$ different nucleic acid molecules of a member of the same species as the mammal to be treated (e.g., an alloexpression library). For example, when treating lung cancer in human A, normal lung tissue from human B can be obtained and used to make a human lung tissue cDNA library that can be administered to human A. In some cases, a nucleic acid library can be a collection of at least about $10^2$ different nucleic acid molecules of a member of a mammalian species that is different from the species of the mammal to be treated (e.g., a xenoexpression library). For example, when treating prostate cancer in a human, normal prostate tissue from a non-human mammal (e.g., a monkey, dog, cat, cow, pig, sheep, goat, mouse, or rat) can be obtained and used to make a non-human mammalian prostate tissue cDNA library that can be administered to the human.

Any appropriate method can be used to make a nucleic acid library. For example, common molecular cloning and PCR techniques can be used to make a cDNA library designed to express the cDNA molecules. Any appropriate method can be used to deliver a nucleic acid library (e.g., an expression nucleic acid library) to a mammal. For example, a nucleic acid library can be delivered as plasmids or can be incorporated into viruses (e.g., oncolytic viruses such as vesicular stomatitis viruses, vaccinia viruses, or adenovirus viruses), bacteria, or cells that are delivered to a mammal. Examples of viruses that can be used to deliver nucleic acid libraries to mammals having cancer include, without limitation, vesicular stomatitis viruses, adenoviruses, vaccinia virusus, retroviruses, and lentiviruses.

Any appropriate method can be used to administer a nucleic acid library to a mammal having cancer. For example, a nucleic acid library can be in the form of plasmids that are formulated with a pharmaceutically acceptable carrier to create a pharmaceutical composition for administration to a human with cancer. In some cases, a nucleic acid library can be in the form of a population of viruses (e.g., a population of vesicular stomatitis viruses) that are formulated with a pharmaceutically acceptable carrier to create a pharmaceutical composition for administration to a human with cancer. In these cases, each virus member of the population of viruses can contain a different nucleic acid member of the nucleic acid library. Examples of pharmaceutically acceptable carriers include, without limitation, liposomes and other lipids. The pharmaceutical composition can include an adjuvant such as HSP70 polypeptides (GenBank gi nos. 38327039 or 38327038), BCG (Bacillus Calmette-Guérin), or Coley's toxin. In some cases, a pharmaceutical composition containing a nucleic acid library can lack serum (e.g., bovine serum such as fetal calf serum).

A nucleic acid library (e.g., population of viruses containing the library) or a composition containing a nucleic acid library can be administered directly to cancer cells (e.g., by intratumoral administration) or can be administered systemically (e.g., by intravenous, intraperitoneal, intrapleural, or intra-arterial administration). Any appropriate amount of material can be administered to a mammal. For example, the amount of material administered to a mammal can be large enough to deliver at least one copy of each nucleic acid member of the nucleic acid library. For example, when using a library that has $10^4$ nucleic acid members incorporated into viruses, then the total number of viruses administered to the mammal can be range from about $10^4$ to about $10^8$. In some cases, the amount of material administered to a mammal can be an amount that is less than the amount needed to deliver at least one copy of each nucleic acid member of the nucleic acid library. For example, when using a library that has $10^6$ nucleic acid members incorporated into viruses, then the total number of viruses administered to the mammal can be range from about $10^4$ to about $10^5$.

The invention will be further described in the following examples, which do not limit the scope of the invention described in the claims.

EXAMPLES

Example 1—Use of Organ-Specific cDNA Libraries Expressed by Oncolytic Viruses to Treat Cancer cDNA libraries from human prostate tissue and mouse prostate recurrent tumors were amplified by PCR and cloned into vesicular stomatitis virus (VSV) (FIG. 1). Briefly, the cDNA library was amplified with primers to allow for directional cloning into the VSV genome between the Xho1 and Nhe1 restriction sites between the G and L genes. Viruses were generated by co-transfection of Vero cells with the viral helper genes and the vaccinia encoded T7 polymerase. Viruses were harvested from transfected cells after 48-72 hours, and all the viruses were amplified for one or two rounds on Vero cells. Viral titers of $10^7$ to $10^8$ pfu/mL were obtained (as tittered on BHK cells by limiting dilution assay). While not being limited to any particular mode of action, it is possible that the viral-expressed cDNA library may encompass epitopes from most normal antigens that might serve as immunogens for cancer rejection, thereby dispensing with the need for direct killing of the normal tissue. In addition, the immunogenicity of the VSV itself could serve the role of an adjuvant.

Figure 2:
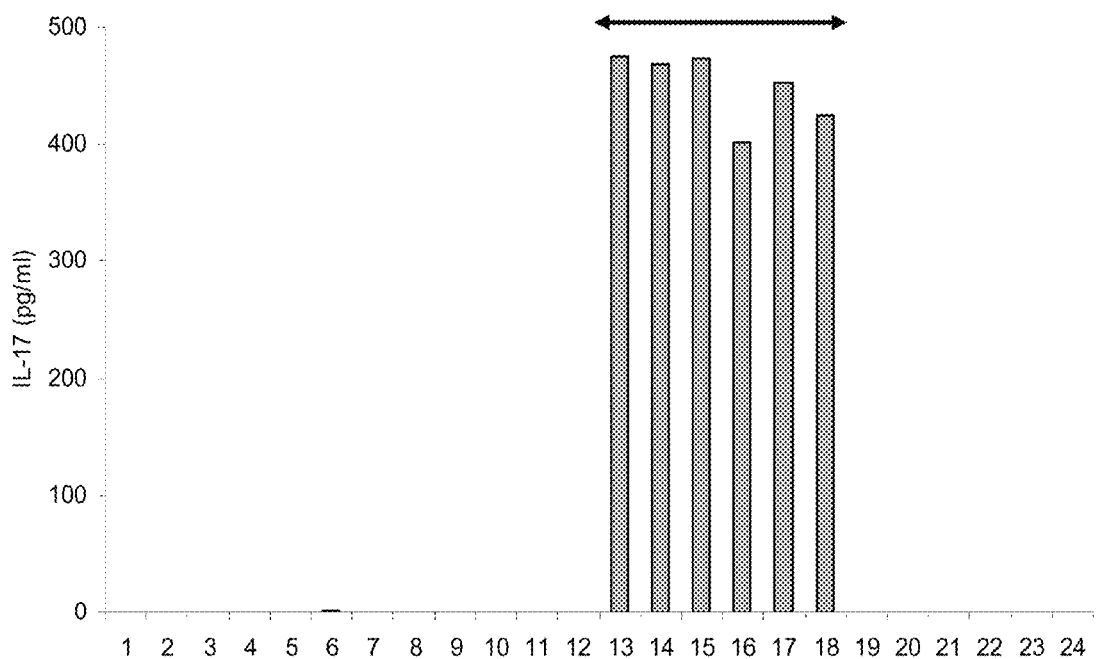
FIG. 2 contains two graphs plotting the level of IL-17 (pg/mL) or IFN-γ (pg/mL) produced by splenocytes from the indicated mice following incubation with TC2 cells (E:T ratio=100:1). Vesicular stomatitis viruses containing a human prostate cDNA library are referred to generally as OSOVIASAL (organ specific oncolytic virus incorporated altered specific antigen library). Lanes 1-3 are results from splenocytes from mice injected intra-prostatically with PBS. Lanes 4-6 are results from splenocytes from mice injected with PBS. Lanes 7-12 are results from splenocytes from mice injected with VSV-GFP. Lanes 13-18 are results from splenocytes from mice injected with OSOVIASAL. Lanes 19-21 are results from TC2 tumor cells only.
Figure 2:
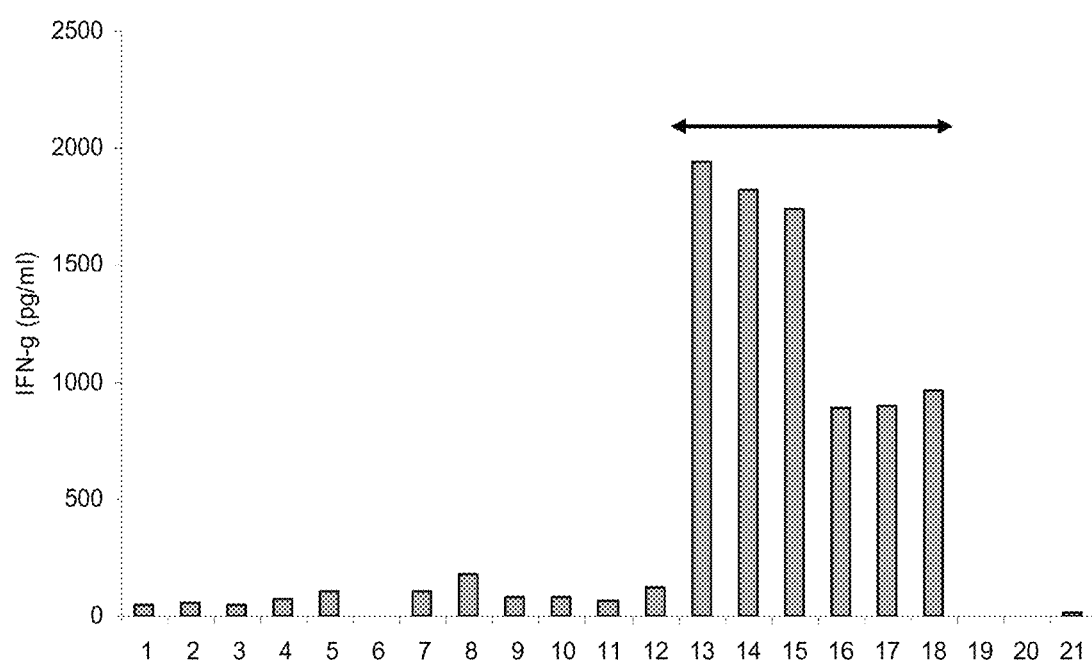

For this study, a total of 18 mice were used. Three mice were used in each group (A1, A2, B1, B2, C1, and C2). The A1 and A2 mice were injected intra-prostatically with PBS. B1 and B2 mice were injected intraprostatically with vesicular stomatitis virus designed to express green fluorescent protein (VSV-GFP). C1 and C2 mice were injected intraprostatically with vesicular stomatitis viruses containing the human prostate cDNA library (VSV-Ag). Each mouse was given 50 µL of virus diluted in PBS at a final titer of ~$10^6$ virus per injection intravenously for a total of 6 injections separated by two days each. The mice were sacrificed on day 40-60 after tumor seeding, and the T-cell splenocytes were evaluated for release of IL-17 (interleukin-17) and IFNγ (interferon-gamma) when co-cultured with TC2 tumor cells. The secretion of significant levels of cytokine in response to stimulation with TC2 cells indicated that the splenocytes contained reactive T cell subsets with specificity for prostate tumor cells. Only the splenocytes from mice injected with VSV-Ag exhibited reactivity to the TC2 murine prostate cancer cells (FIG. 2).

Figure 3:
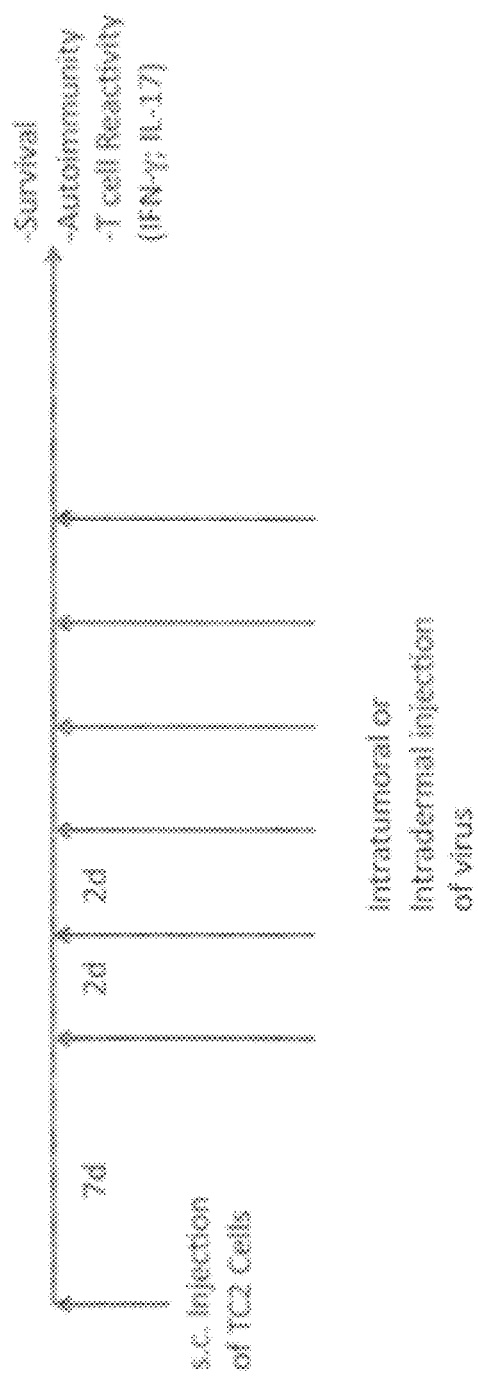
FIG. 3 is a diagram of an administration protocol for testing the use of a nucleic acid library to treat cancer.

In an in vivo study, 35 mice were injected with TC2 prostate cancer cells subcutaneously (sc) on day one. When the sc prostate cancer was palpable, at about day 7, the mice were divided into five groups (A, B, C, D, and E) of mice with seven mice in each group, and the following injections were performed (FIG. 3): intratumoral injection of VSV-GFP (Group A), intratumoral injection of VSV-Ag (OSOVIASAL of the human prostate antigen library; Group B), intratumoral injection of VSV-GFP HI (heat inactivated; Group C), intravenous injection of VSV-Ag (Group D), and intravenous injection of VSV-GFP (Group E). Injections were performed every two days for a total of six injections. The mice were evaluated for survival and autoimmunity, and at the time of sacrifice, the T cells (splenocytes) were evaluated for reactivity via release of IL-17 and IFNγ.

Figure 4:
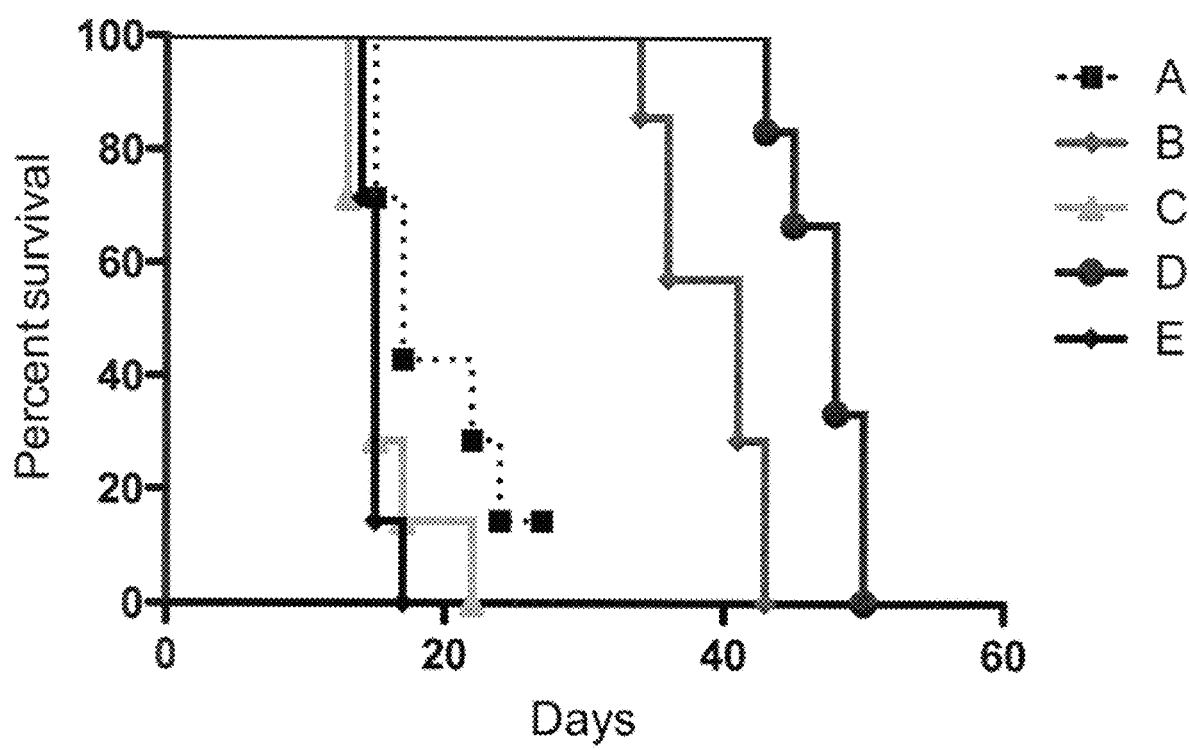
FIG. 4 is a graph plotting survival curves for mice with subcutaneous TC2 prostate cancer and treated as indicated for Groups A, B, C, D, and E. Each group contained seven mice.

Kaplan-Meyer survival curves revealed a marked difference in survival in Groups B and D (VSV-Ag given either intratumorally or intravenously) than for the other groups (FIG. 4). The 50% survival time was about 20 days for the other groups, while it was about 40 days for Group B (intratumoral VSV-Ag) and about 50 days for Group D (VSV-Ag iv). Histology of the tumors revealed marked tumor regression in Groups B and D with minimal signs of autoimmune prostatitis (FIGS. 6-9).

Figure 5:
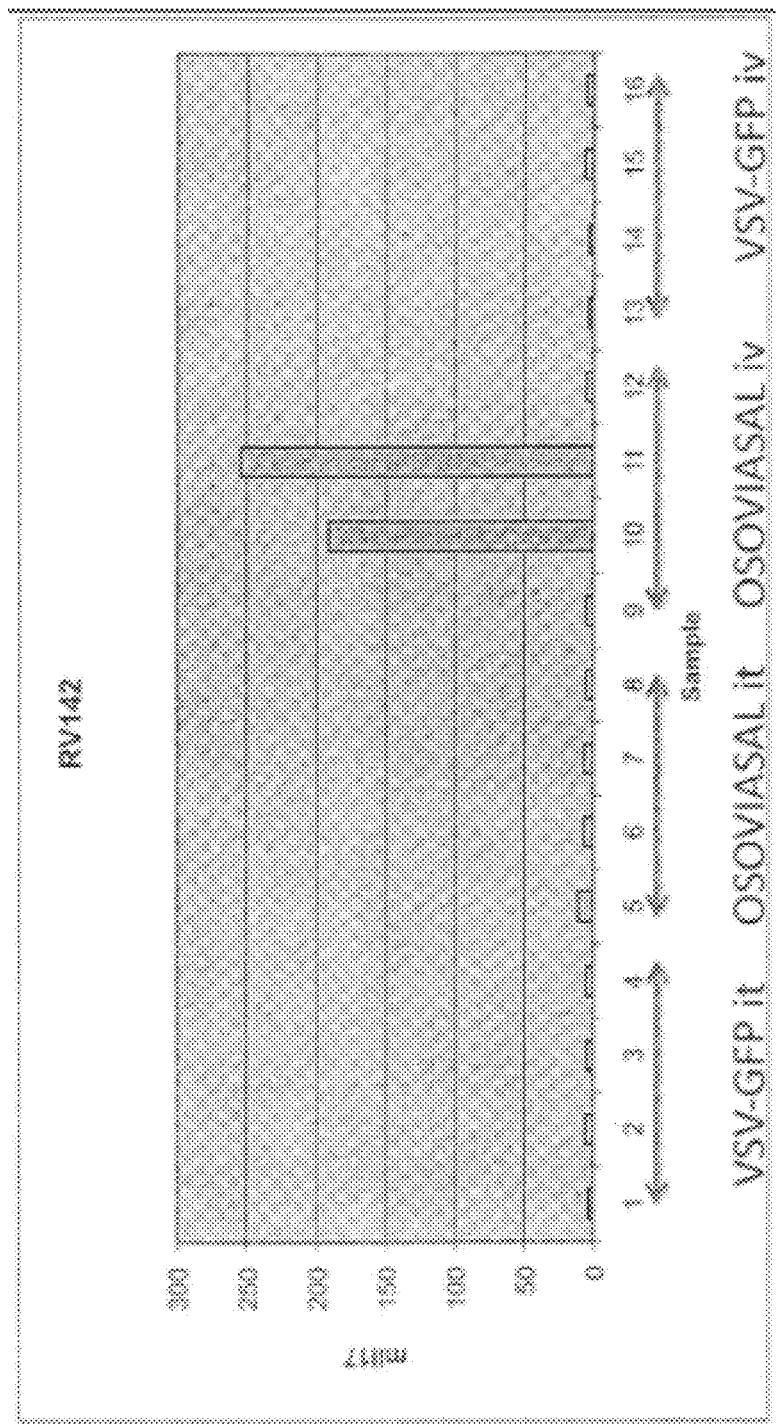
FIG. 5 is a graph plotting the level of IL-17 (pg/mL) produced by splenocytes from mice treated as indicated following incubation with either a B16 melanoma lysate (lanes 1, 5, 9, and 13), a TrampC2 prostate tumor lysate (lanes 2, 6, 10, and 14), a normal mouse prostate lysate (lanes 3, 7, 11, and 15), or a normal mouse pancreas lysate (lanes 4, 8, 12, and 16). No difference was observed in the level of IFNγ between these groups. it=intratumoral injections; iv=intravenous injections.
Figure 6:
FIG. 6 contains photographs (4×) of TC2 tumors following intravenous treatment with VSV-GFP or OSOVIASAL, which induced tumor regression with minimal signs of autoimmune prostatitis. The TC2 tumors that underwent regression and regrowth in vivo exhibited a very different morphology from VSV-GFP- or control-treated TC2 tumors.
Figure 6:
Figure 7:
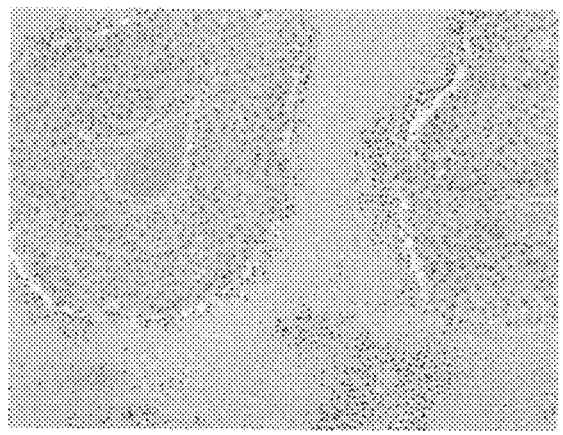
FIG. 7 contains photographs (10×) of TC2 tumors following intravenous treatment with VSV-GFP or OSOVIASAL, which induced tumor regression with minimal signs of autoimmune prostatitis.
Figure 7:
Figure 8:
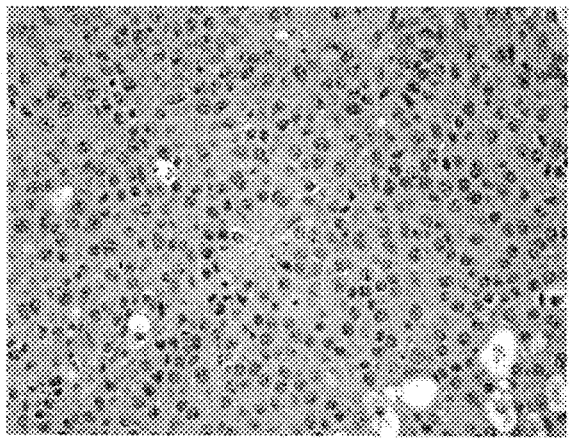
FIG. 8 contains photographs of TC2 tumors following intravenous treatment with VSV-GFP or OSOVIASAL, which induced tumor regression with minimal signs of autoimmune prostatitis.
Figure 8:
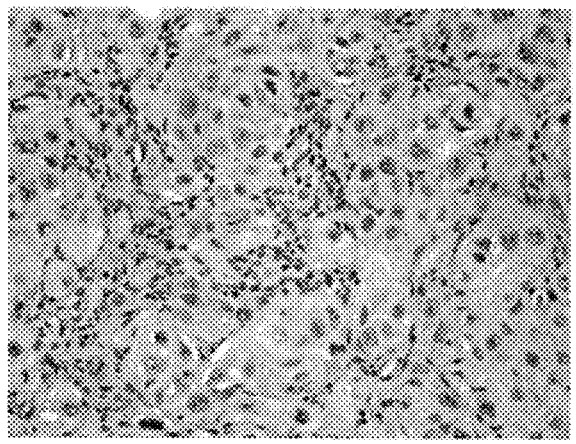
Figure 9A:
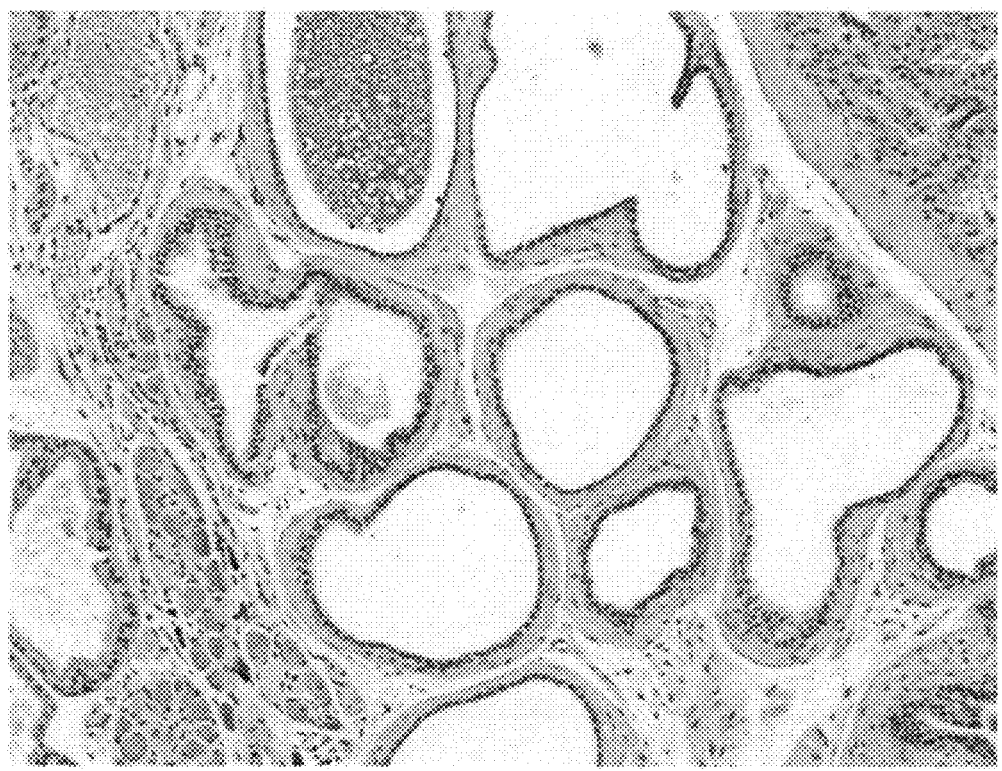

Reactivity of the splenocytes from four mice each from Group A, Group B, Group D, and Group E were tested against B16 melanoma lysate targets, TC2 protstate tumor lysate targets, normal mouse prostate lysate targets, and normal mouse pancreas lysate targets. Only Group D exhibited reactivity to TC2 lysate with release of IL-17 (FIG. 5). These results demonstrate that an altered self-antigen expression via viruses expressing a nucleic acid library can cause reaction to the cancer but not to normal tissues or other cancers. These results also demonstrate that expression of nucleic acid libraries can be used to treat cancer (e.g., prostate cancer).

In summary, injection (e.g., intravenous) of VSV encoding a cDNA library from normal prostate resulted in regression of murine prostate tumors in immune competent mice. The regressions were immune mediated, as opposed to induced by viral oncolysis. Transient inflammation was observed in the normal prostate, but no evidence of long term autoimmunity was apparent. Mice in which tumors were rejected developed potent Th17 responses against prostate tumor cells, as well as normal prostate tissues. Moreover, tumors which initially regressed, but were not cured, recurred aggressively, with a markedly different histological appearance, and antigenic profile, to the initially implanted tumor cells, suggesting that the cDNA library-mediated vaccination imposed a stringent immune selection upon tumors. This approach dispensed with the need to induce direct damage to normal tissues in situ, allowed for wide-ranging in vivo immune selection for antigens that are likely to be effective targets for both autoimmune and anti-tumor responses, and established the use of viruses (e.g., oncolytic viruses) as immune adjuvants for the immunotherapy of cancer. The results provided herein further demonstrate that combining induction of autoimmune reactivity against normal tissue-specific antigens (e.g., polypeptides) with highly immunogenic, viral adjuvant-induced antigen presentation can be a successful cancer immunotherapy.

Figure 10:
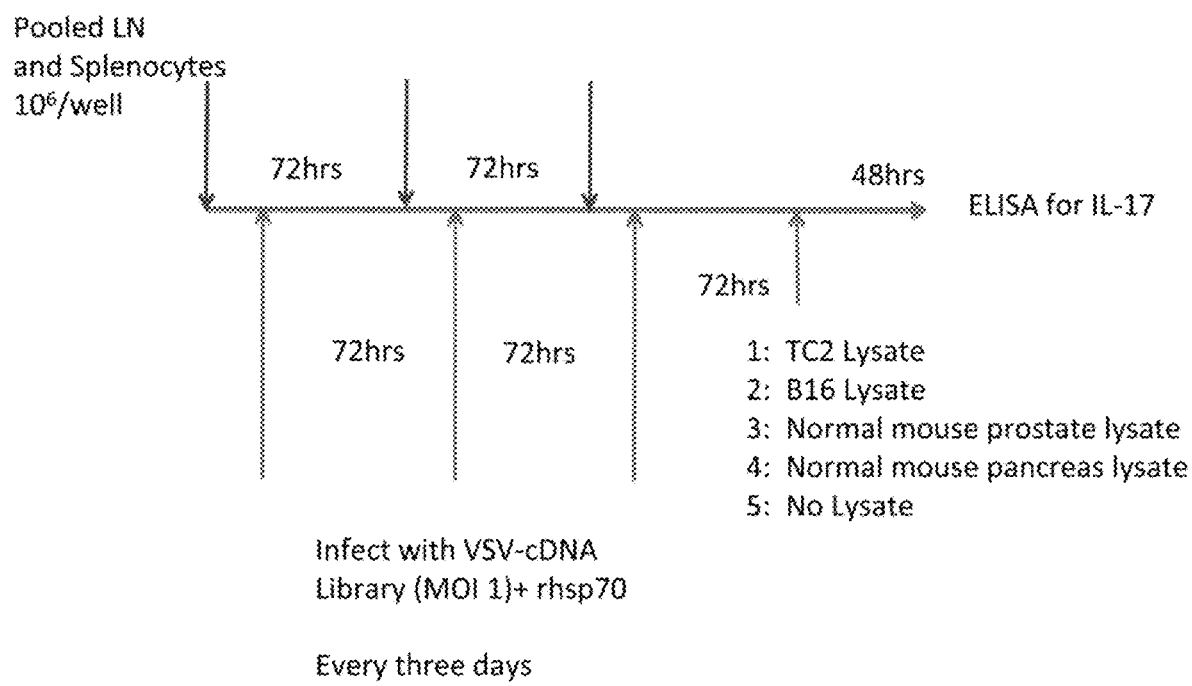
FIG. 10 is a diagram of an experiment designed to assess the ability of OSOVIASAL in combination with recombinant HSP70 to stimulate IL-17 release.
Figure 11:
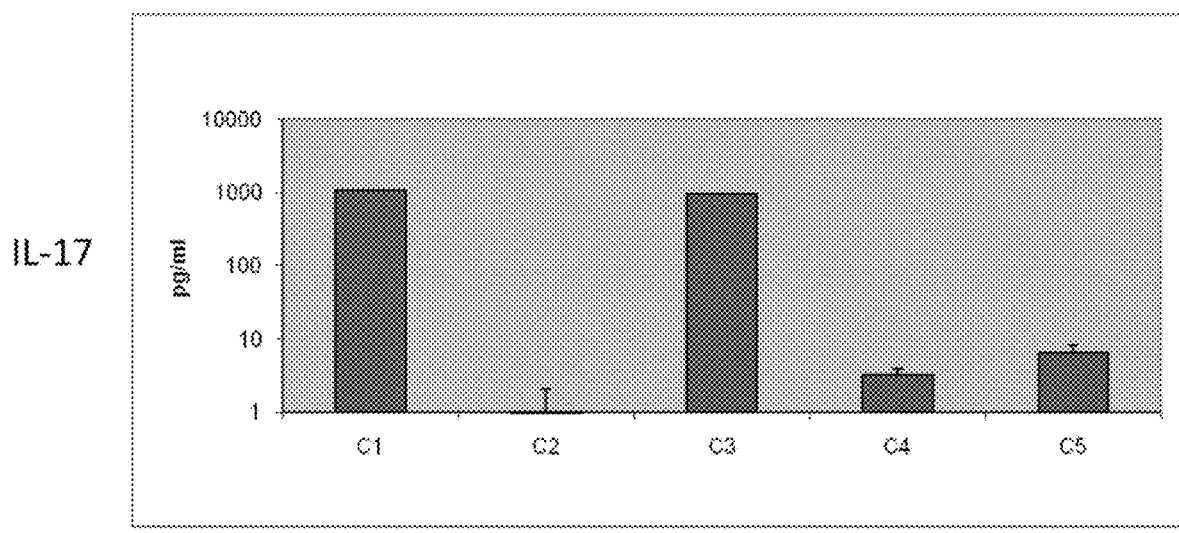
FIG. 11 is a graph plotting the amount of IL-17 released (pg/mL) from splenocytes and lymph node cells infected with OSOVIASAL in the presence of recombinant HSP70 following exposure to a prostate cancer cell lysate (TC2 cell lysate; C1), a melanoma cell lysate (B16 cell lysate; C2), a normal mouse prostate cell lysate (C3), a normal mouse pancreas cell lysate (C4), or no lysate (C5).

Example 2—Use of a Heat Shock Protein, HSP70, in Combination with Organ-Specific cDNA Libraries Expressed by Oncolytic Viruses to Treat Cancer Vesicular stomatitis viruses containing a cDNA library from human prostate tissue (OSOVIASAL of the human prostate antigen library) was used in combination with recombinant HSP70 (Sigma-Aldrich, St Louis, Product #H7283) to assess the combination's ability to increase IL-17 responses. Briefly, pooled lymph node cells and splenocytes from C57BL/6 mice were plated $10^6$ cells per well. After an incubation, the cells were infected with the vesicular stomatitis viruses containing the cDNA library from human prostate tissue (MOI=1) in the presence of 10 µg/mL of recombinant HSP70. 72 and 144 hours after the initial plating, additional cells ($10^6$ cells per well) were added to each well (FIG. 10). In addition, 72 and 144 hours after the initial infection, additional infections in the presence of recombinant HSP70 were carried out (FIG. 10). 72 hours after the third infection, the cells were incubated with (a) a prostate cancer cell lysate (TC2 cell lysate), (b) a melanoma cell lysate (B16 cell lysate), (c) a normal mouse prostrate cell lysate, (d) a normal mouse pancreas cell lysate, or (e) no lysate, for 48 hours. After the 48-hour incubation, the cells were assessed by ELISA for IL-17 release. Lysates from prostate cancer cells and normal prostate cells caused a marked IL-17 response in splenocytes as compared to the response measured for cells exposed to the other lysates (FIG. 11). These results demonstrate that the addition of HSP-70 to VSV expressing cDNAs to prostate increased the IL-17 autoimmune response to both tumor and normal organ tissues.

Example 3—Use of a Tumor-Specific cDNA Library Expressed by Oncolytic Viruses to Treat Cancer A cDNA library was made using nucleic acid from mouse B16ova melanoma tumor cells and cloned into vesicular stomatitis virus (VSV). The VSV library was designated OSOVITAL-ova.

In an in vivo study, C57BL/6 mice were injected with B16ova melanoma tumor cells subcutaneously (sc) on day one. When the subcutaneous melanoma cancer was palpable, the mice were divided into two groups (OSOVITAL-ova and VSV-GFP) of mice with seven mice in each group, and the following injections were performed: intratumoral injection of OSOVITAL-ova and intratumoral injection VSV-GFP. Injections were performed every two days for a total of six injections. The mice were evaluated for survival.

Figure 12:
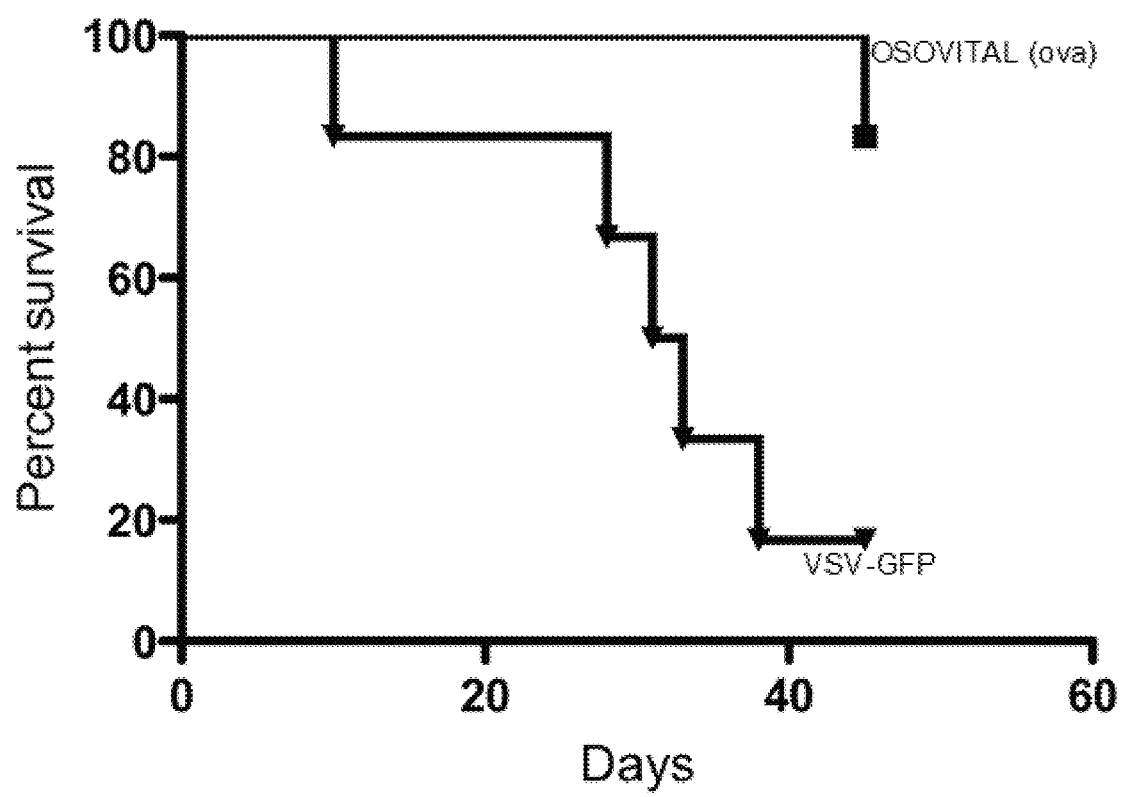
FIG. 12 is a graph plotting survival curves for mice with subcutaneous B16ova melanoma cancer and treated with OSOVITAL-ova or VSV-GFP.

Kaplan-Meyer survival curves revealed a marked difference in survival for mammals treated with OSOVITAL-ova as compared to mammals treated with VSV-GFP (FIG. 12). These results demonstrate that cDNA libraries from cancer cells constructed in a virus such as VSV can induce significant responses against cancer cells present within a mammal.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition for treating cancer present in a mammal, wherein said composition comprises a nucleic acid library comprising a plurality of different nucleic acid members, wherein each of said plurality of different nucleic acid members encodes a different mammalian polypeptide and is located within the genome of an oncolytic virus having the ability to infect a cell present within said mammal, and wherein said mammalian polypeptides are expressed within said mammal following administration of said composition to said mammal.

2. The composition of claim 1, wherein said mammal is a human.

3. The composition of claim 1, wherein said administration is an intratumoral or intravenous administration.

4. The composition of claim 1, wherein said nucleic acid library is a cDNA library.

5. The composition of claim 1, wherein said oncolytic virus is a vesicular stomatitis virus.

6. The composition of claim 1, wherein said different mammalian polypeptides are polypeptides of a member of the same species as said mammal.

7. The composition of claim 1, wherein said different mammalian polypeptides are polypeptides of a member of a different species than the species of said mammal.

8. The composition of claim 1, wherein said different mammalian polypeptides are polypeptides of said mammal.

9. The composition of claim 1, wherein said different mammalian polypeptides are polypeptides of said cancer.

10. The composition of claim 1, wherein said different mammalian polypeptides are polypeptides of an organ or tissue that is an organ or tissue of origin of said cancer.

11. The composition of claim 1, wherein said cancer is prostrate cancer, and said different mammalian polypeptides are polypeptides expressed by prostate cells.

12. The composition of claim 1, wherein said cancer is lung cancer, and said different mammalian polypeptides are polypeptides expressed by lung cells.

13. The composition of claim 1, wherein said cancer is skin cancer, and said different mammalian polypeptides are polypeptides expressed by skin cells.

14. The composition of claim 1, wherein said nucleic acid library comprises a collection of greater than $10^4$ different nucleic acid members, and wherein each of said $10^4$ different nucleic acid members encodes a different mammalian polypeptide.

15. The composition of claim 1, wherein said nucleic acid library comprises a collection of greater than $10^5$ different nucleic acid members, and wherein each of said $10^5$ different nucleic acid members encodes a different mammalian polypeptide.

16. The composition of claim 1, wherein said nucleic acid library comprises a collection of greater than $10^6$ different nucleic acid members, and wherein each of said $10^6$ different nucleic acid members encodes a different mammalian polypeptide.

17. The composition of claim 1, wherein said nucleic acid library comprises a collection of greater than $10^7$ different nucleic acid members, and wherein each of said $10^7$ different nucleic acid members encodes a different mammalian polypeptide.

18. The composition of claim 1, wherein said composition lacks serum.

* * * * *

UNITED STATES PATENT AND TRADEMARK OFFICE
CERTIFICATE OF CORRECTION

PATENT NO. : 10,849,964 B2
APPLICATION NO. : 16/011416
DATED : December 1, 2020
INVENTOR(S) : Richard G. Vile et al.

Page 1 of 1

It is certified that error appears in the above-identified patent and that said Letters Patent is hereby corrected as shown below:

In the Claims

In Claim 11, delete "prostrate" and insert -- prostate --, therefor.

Signed and Sealed this
Twenty-second Day of October, 2024

Katherine Kelly Vidal
*Director of the United States Patent and Trademark Office*